US009750530B2

(12) United States Patent
Imai et al.

(10) Patent No.: US 9,750,530 B2
(45) Date of Patent: Sep. 5, 2017

(54) EPIDURAL SPACE IDENTIFICATION DEVICE

(71) Applicant: FORCE ENGINEERING CO., LTD., Utsunomiya-shi, Tochigi (JP)

(72) Inventors: Takanori Imai, Utsunomiya (JP); Hiroshi Hirota, Nasushiobara (JP)

(73) Assignee: FORCE ENGINEERING CO., LTD., Utsunomiya-Shi (JP)

(*) Notice: Subject to any disclaimer, the term of this patent is extended or adjusted under 35 U.S.C. 154(b) by 317 days.

(21) Appl. No.: 14/405,075

(22) PCT Filed: Jun. 25, 2014

(86) PCT No.: PCT/JP2014/066806
§ 371 (c)(1),
(2) Date: Dec. 2, 2014

(87) PCT Pub. No.: WO2015/052963
PCT Pub. Date: Apr. 16, 2015

(65) Prior Publication Data
US 2016/0262792 A1    Sep. 15, 2016

(30) Foreign Application Priority Data
Oct. 7, 2013 (JP) .................... 2013-209969

(51) Int. Cl.
*A61B 17/34*    (2006.01)
*A61M 19/00*    (2006.01)
(Continued)

(52) U.S. Cl.
CPC .......... *A61B 17/3401* (2013.01); *A61B 90/08* (2016.02); *A61M 5/31505* (2013.01);
(Continued)

(58) Field of Classification Search
CPC ... A61B 17/3401; A61B 90/08; A61B 5/4896; A61M 5/31505; A61M 5/14; A61M 19/00
See application file for complete search history.

(56) References Cited

U.S. PATENT DOCUMENTS 4,215,699 A     8/1980  Patel
4,624,659 A *  11/1986  Goldberg .............. A61M 5/486
                                                      222/47
(Continued)

FOREIGN PATENT DOCUMENTS

JP    H08-501478 A     2/1996
JP    2006-516436 A    7/2006
(Continued)

OTHER PUBLICATIONS

Sep. 22, 2014 Translation of International Search Report issued in International Application No. PCT/JP2014/066806.
(Continued)

*Primary Examiner* — Kami A Bosworth
*Assistant Examiner* — Alexandra Lalonde
(74) *Attorney, Agent, or Firm* — Oliff PLC

(57) ABSTRACT

An epidural space identification device to identify when a tip of a needle used for epidural anesthesia enters an epidural space that includes a barrel formed in a cylindrical shape and communicatively connected to a needle section, a plunger formed in a cylindrical shape, retractably inserted into the barrel, and having an air hole communicating with an inside of the plunger, and an expansible member having an expansible part provided at a front end part of the plunger and bulging inside of the plunger with a positive pressure generated by pushing the plunger while air discharge from a needle side is regulated.

6 Claims, 2 Drawing Sheets

(51) Int. Cl.
*A61M 5/315* (2006.01)
*A61M 5/46* (2006.01)
*A61B 90/00* (2016.01)

(52) U.S. Cl.
CPC .............. *A61M 5/46* (2013.01); *A61M 19/00* (2013.01); *A61B 2090/0807* (2016.02); *A61M 2205/3344* (2013.01)

(56) References Cited

U.S. PATENT DOCUMENTS

| | | | |
|---|---|---|---|
| 5,300,046 | A | 4/1994 | Scarfone et al. |
| 5,902,273 | A | 5/1999 | Yang et al. |
| 7,175,608 | B2 | 2/2007 | Hasan et al. |
| 8,137,312 | B2 * | 3/2012 | Sundar ............... A61B 17/3401 604/121 |
| 2004/0186430 | A1 | 9/2004 | Hasan et al. |
| 2007/0142766 | A1 | 6/2007 | Sundar et al. |
| 2008/0132926 | A1 | 6/2008 | Eichmann et al. |
| 2013/0085413 | A1 * | 4/2013 | Tsamir ................ A61B 5/0053 600/567 |

FOREIGN PATENT DOCUMENTS

| | | |
|---|---|---|
| JP | 2010-511442 A | 4/2010 |
| JP | 4810421 B2 | 11/2011 |

OTHER PUBLICATIONS

Sep. 22, 2014 Translation of Written Opinion of the International Searching Authority issued in International Application No. PCT/JP2014/066806.

\* cited by examiner

EPIDURAL SPACE IDENTIFICATION DEVICE

This is the National Stage filing under 35 U.S.C. 371 of the International Application PCT/JP2014/066806, filed Jun. 25, 2014, which claims priority under 35 U.S.C. 119 (a-d) to JP 2013-209969, filed Oct. 7, 2013.

TECHNICAL FIELD

The present invention relates to the technical field of a device to identify when a needle enters the epidural space in operation of epidural anesthesia for surgery, obstetric surgery, etc. as an analgesic treatment.

BACKGROUND ART

In general, epidural anesthesia has increasingly been adopted in various analgesic treatments for surgery, obstetric surgery, etc. In the epidural anesthesia, it is necessary to ascertain whether a tip of the needle enters the epidural space (cavity) in the spinal column. The epidural space is located across the rigid ligamentum flavum. Therefore, it is commonly practiced that, when a Touhy needle is inserted into the spinal column, the operator identifies when the needle tip enters the epidural space across the ligamentum flavum by sensing a loss of resistance coming from the needle after passing through the rigid ligamentum flavum where the needle receives resistance. Such operations require that the anesthetist be highly experienced and is capable of performing highly proficient techniques.

Then, there is a disclosure where an injection device is used to identify when a needle tip enters the epidural space. In the disclosure, a plunger is movably disposed in a syringe, and the plunger is being withdrawn toward the end of the syringe to bias a spring while the needle is inserted into the spinal column. When the needle tip enters the epidural space across the ligamentum flavum, the resistance of the ligamentum flavum is lost, and accordingly the plunger advances toward the front end of the syringe by the biased spring. Thereby, the entering of the needle tip into the epidural space is identified by the movement of the plunger (see Patent Document No. 1).

However, the injection device requires not only the special syringe and plunger but also the spring. These requirements increase the number of components and makes the structure complex.

Another disclosure shows a device that identifies when a needle tip enters into the epidural space. The device includes an air inlet opening where air inflows from a syringe, an air output opening where the air outflows into the needle in which the air flow is into the epidural space, and a membrane (diaphragm, gasket) that bulges by a pressurized air flow from the air inlet opening while the air supply opening is closed. And after the needle is inserted into the back of the patient or into the ligamentum flavum where the resistance is given to the needle, the pressurized air is supplied from the syringe to bulge the membrane. Then the needle is inserted farther toward a spinal column, and when the needle tip enters into the epidural space, the bulged membrane shrinks and flattens as the pressurized air in the membrane flows into the epidural space (see Patent Document 2).

RELATED ART DOCUMENTS

Patent Documents

Patent Document 1: Japanese Patent No. 4810421
Patent Document 2: U.S. Pat. No. 7,175,608

SUMMARY OF THE INVENTION

Problems to be Solved by the Invention

However, the Patent Document 2 has problems that since the membrane is exposed outside, it is prone to be damaged when surgical instruments such as needles or surgical knives are accidentally touched to it. Moreover, the number of components also increases as it requires a special tool to install the membrane to the device and the syringe to provide air into the device. These are the problems to be solved by the present invention.

Means for Solving the Problems

In view of the circumstances discussed above, the present invention was made to resolve the problems, and the invention of a first aspect provides an epidural space identification device to identify when a tip of a needle used for epidural anesthesia enters an epidural space, comprising a barrel formed in a cylindrical shape, and communicatively connected to a needle section, a plunger formed in a cylindrical shape, retractably inserted into the barrel, and having an air hole communicating with an inside of the plunger, and an expansible member having an expansible part provided at a front end part of the plunger and bulging inside of the plunger with a positive pressure generated by pushing the plunger while air discharge from a needle side is regulated.

The invention of a second aspect provides the epidural space identification device according to the first aspect, wherein the expansible member further comprises an outer circumferential part that fits to an outer circumferential surface of the front end part of the plunger and slidably contacts to an inner circumferential surface of the barrel, an engagement protrusion that engages with an engagement groove formed on the outer circumferential surface of the front end part of the plunger, and a proximal end part (4c) that contacts to the front end part of the plunger, and the expansible part that bulges inside of the plunger is continuous with the proximal end part.

The invention of a third aspect provides the epidural space identification device according to the first or second aspect, wherein the expansible part is provided on a base end of a cylindrical inner part formed at an inner end of the proximal end part so that the cylindrical inner part fits to an inner circumferential surface of the plunger.

The invention of a fourth aspect provides the epidural space identification device according to any one of the first through third aspects, wherein the air hole is formed at a base end surface of the plunger.

Effects of the Invention

According to the invention of the first aspect, an expansible part that bulges with the positive pressure generated by pushing the plunger is placed to bulge inside the plunger so as not to expose the expansible part to the outside of the barrel. Consequently, the expansible part is reliably protected and not damaged by touching any medical instruments such as needles. Further, since the plunger is also used as a holding member of the expansible member, there is no need to prepare another holding member separately, and accordingly the reduction of the number of components is achieved.

According to the invention of the second aspect, it becomes easy and secure to fit the expansible member to the plunger.

According to the invention of the third aspect, as the position of the expansible part is located toward the base end side of the plunger from the front end side thereof, the bulging state of the expansible part can be easily recognized.

According to the invention of the fourth aspect, it is easy to form the air hole on the plunger that functions as a vent for the escape of air from the plunger when the expansible member bulges.

MODES FOR CARRYING OUT THE INVENTION

An embodiment of the present invention will be discussed as follows with reference to the drawings.

Figure 1:
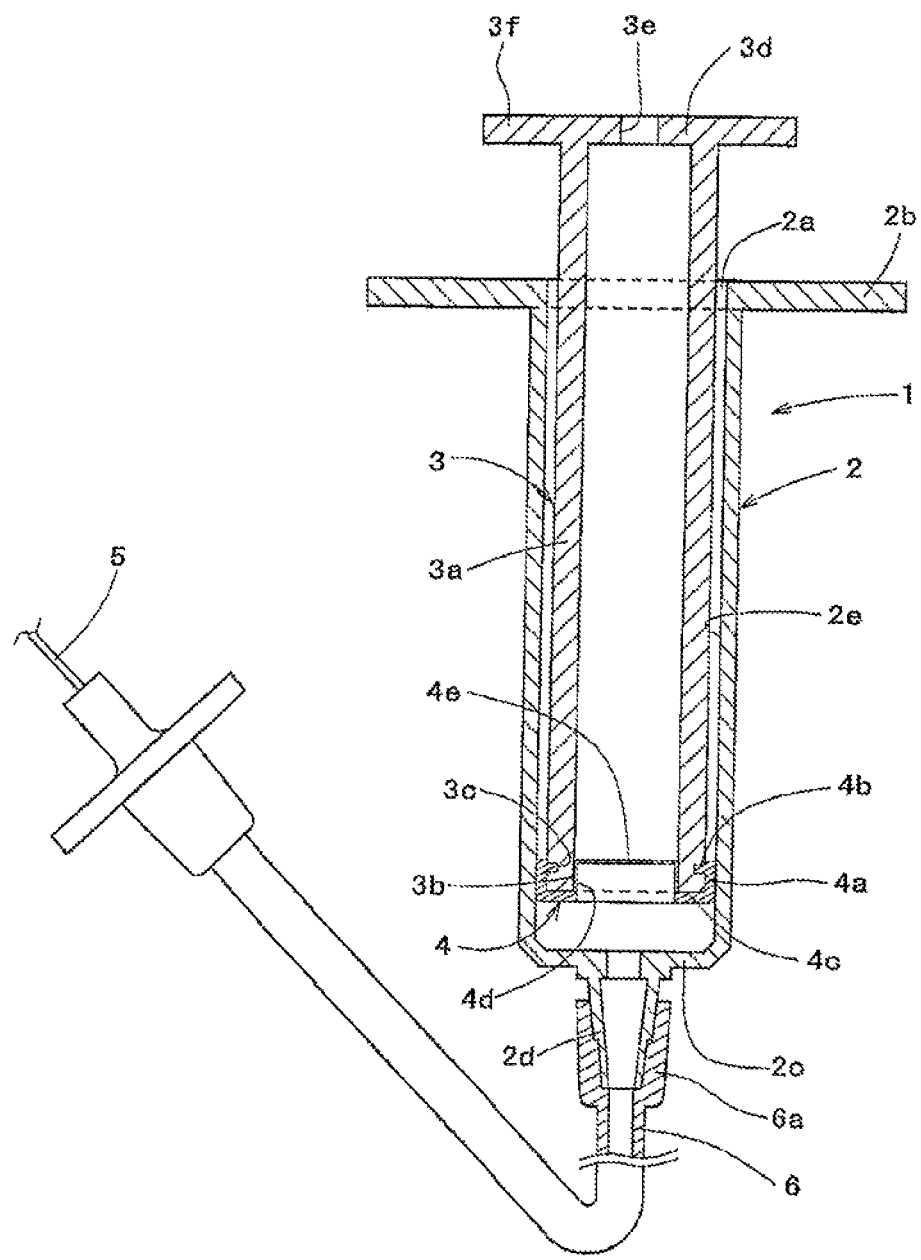
FIG. 1 is a cross-sectional view of an epidural space identification device before an expansible member bulges.

In FIG. 1, a syringe 1 is used for the identification of the epidural space. The syringe 1 comprises a cylindrical barrel 2, a plunger 3 that is retractably inserted into the barrel 2, and an expansible member (diaphragm, gasket) 4 that is fitted onto the plunger 3. A base end 2a of the cylindrical barrel 2 is opened, and a flange part 2b is formed on the barrel 2. A front end of the cylindrical barrel 2 is closed and a bottom part 2c is formed at the front end, and a luer taper part 2d is formed at the bottom part 2c, where a base end part 6a of a tube 6 engages detachably, the tube 6 is connected to a needle 5 used for the insertion into the epidural space.

The plunger 3 includes a hollow cylindrical part 3a that fits loosely or slidably inside the barrel 2 (In this embodiment, the plunger fits to the barrel loosely.). A front end part 3b of the cylindrical part 3a is opened and an engagement groove 3c is formed on an outer circumferential surface of the front end part 3b. On the other hand, a base end side 3d is closed except for an air hole 3e formed to communicate with the cylindrical part 3a, and a flange part 3f is formed around the base end side 3d.

The expansible member 4 is made of rubber elastic material such as silicone rubber or natural rubber, etc. An outer circumferential part 4a of the expansible member 4 fits to an outer surface of the front end part 3b of the plunger 3, and in that state, the outer circumferential part 4a contacts to an inner circumferential surface 2e of the barrel 2 pressing lightly and preventing air leakage between them. The expansible member 4 keeps its posture (motionless) relative to the barrel 2 without there being either push or pull operation of the plunger 3. An engagement protrusion 4b is formed on an inner side surface of the outer circumferential part 4a to engage with the engagement groove 3c of the plunger 3.

A proximal end part 4c that is formed continuously from the outer circumferential part 4a of the expansible member 4 is thick, as is the outer circumferential part 4a, and the proximal end part 4c is fitted to the front end of the plunger 3. A cylindrical inner part 4d that is formed continuously from an inner end of the proximal end part 4c is thin and fits to an inner circumferential surface of the front end part 3b of the plunger 3. A base end part of the cylindrical inner part 4d is approximately at the same level as the outer circumferential part 4a, and an expansible part (diaphragm part) 4e that is expandable is provided on the base end of the cylindrical inner part 4d such that the expansible part 4e seals the base end of the plunger.

Figure 2:
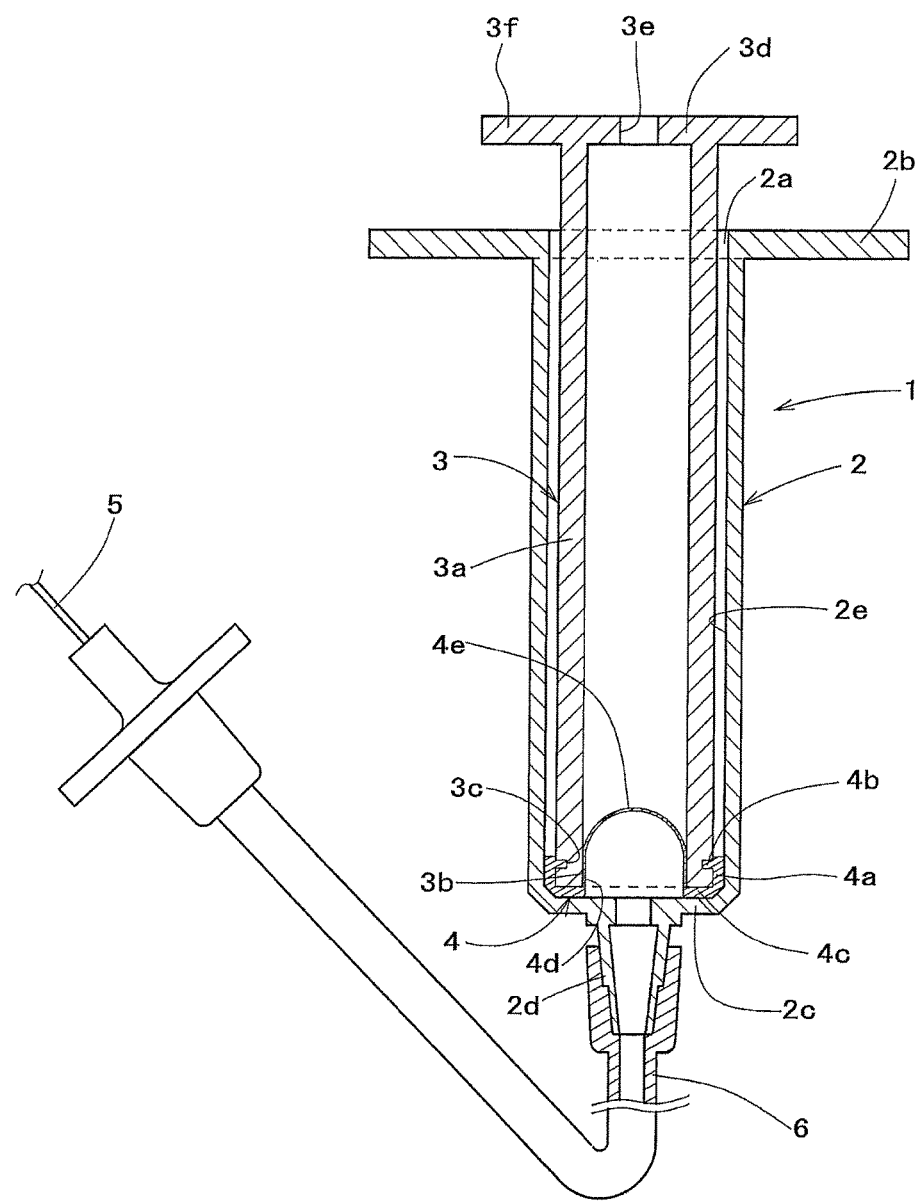
FIG. 2 is a cross-sectional view of an epidural space identification device when an expansible member bulges.

In operation of epidural anesthesia, it is necessary to identify when a tip of the needle 5 enters the epidural space. To identify the epidural space, the plunger 3 is withdrawn toward the base end side of the barrel 2 to draw a required volume of air (1 milliliter, for example), and while holding the plunger 3 in the withdrawn position to the barrel 2, the needle 5 is connected to the syringe 1 communicatively through the tube 6. Then, the needle 5 is inserted into the spinal column, and when the tip of the needle reaches the ligamentum flavum and the resistance from the ligamentum flavum is sensed, the insertion of the needle is suspended. At this point, the tip of the needle 5 is in a blocked state. While maintaining the state, the plunger 3 is pushed into the barrel 2 until the proximal end part 4c touches the bottom part 2c, thereby the expansible part 4e bulges (expands) with the positive pressure, as illustrated in FIG. 2. After that, the insertion of the needle 5 is resumed, and when the tip of the needle enters the epidural space, the air flows into the epidural space, and the expansible part 4e contracts and returns to its original state. The entering of the needle tip into the epidural space is identified by perceiving the phenomenon. After that, epidural anesthesia is operated by removing the syringe 1 from the tube 6 or any other proper way.

In the embodiment of the disclosure structured as described above, in operation of epidural anesthesia, the syringe and the needle 5 are connected while the plunger 3 is being withdrawn to the required volume, then the needle 5 is inserted into the spinal column, and the insertion is suspended at the time the needle tip reaches to the ligamentum flavum. Then the plunger 3 is pushed into the barrel 2 so that the expansible part 4e bulges. After that, the insertion of the needle 5 is resumed, and when the needle tip 5 enters into the epidural space, the positively pressurized air in the bulged expansible part 4e, that is generated by pushing the plunger 3 into the barrel 2, outflows into the epidural space and thereby the bulged expansible part 4e contracts. Therefore, the identification of entering of the needle tip into the epidural space is confirmed by sight, and the operator proceeds with the next step of the epidural anesthesia.

In the above-discussed present embodiment, entering of the needle tip into the epidural space can be identified by recognizing the contraction of the expansible part 4e, and since the expansible part 4e is placed inside the syringe 1, the expansible part 4e is not exposed to the outside, and therefore the expansible part 4e is prevented from the damage caused by touching medical instruments such as needles or surgical knives.

Moreover, as the expansible member 4 is provided inside the syringe 1 that is to supply air, the syringe itself is also used as the expansion device of the expansible member 4. Thus, reduction of the number of components is achieved.

Furthermore, as the supply of the air into the epidural space is performed in the state of the expansible part 4e bulging with the positive pressure, the identification of the location can also be performed reliably to another part of the body that is not negatively pressurized like the epidural space.

Also, in accordance with the disclosure, the expansible member 4 fits onto the outer circumferential part of the front end part 3b of the plunger 3, and the expansible member 4 includes the outer circumferential part 4a that contacts to the inner circumferential surface 2e of the barrel slidably, the engagement protrusion 4b that engages with the engagement groove 3c formed on the outer circumferential part of the front end part 3b of the plunger, and the proximal end part 4c that contacts to the front end part 3b of the plunger 3, and the expansible member 4e is configured to bulge inside of the plunger 3 in the state of being continuous with the proximal end part 4c. Therefore, it is easy and secure to fit the expansible member 4 to the plunger 3. Further, the expansible member 4 moves following the movement of pushing and pulling of the plunger 3.

Furthermore, in accordance with the disclosure, as the expansible part 4e is formed on the base end of the cylindrical inner part 4d that is provided from the inner end of the proximal end part 4c in order to contact closely to the inner circumferential surface of the plunger, the expansible part 4e is located closer to the base end side of the plunger compared to the expansible member, for example, compared to being fitted flatly on the front end of the plunger. Thus, the deformation of the expansible part can be easily visible. Of course, the expansible part 4e can be configured to be formed flat with the proximal end part.

In addition to that, in accordance with the disclosure, the air hole 3e formed on the base end part 3d of the plunger, that functions as a vent for the escape of air from the cylindrical plunger 3a when the expansible part 4e bulges, can be easily processed.

INDUSTRIAL APPLICABILITY

The present invention can be utilized as an epidural space identification device to identify when the tip of the needle enters the epidural space in the operation of the epidural anesthesia.

DESCRIPTION OF REFERENCE NUMERALS 1 syringe
2 barrel
3 plunger
3a cylindrical part
3b front end part
3c engagement groove
3e air hole
4 expansible member
4a outer circumferential part
4b engagement protrusion
4c proximal end part
4d cylindrical inner part
4e expansible part
5 needle

The invention claimed is:

1. An epidural space identification device to identify when a tip of a needle used for epidural anesthesia enters an epidural space, comprising:
   a barrel formed in a cylindrical shape, and communicatively connected to a needle section,
   a plunger formed in a cylindrical shape, retractably inserted into the barrel, and having an air hole communicating with an inside of the plunger, and
   an expansible member that has an expansible part and is provided at a front end part of the plunger, wherein:
      the expansible part bulges inside of the plunger with a positive pressure generated by pushing the plunger while the tip of the needle is in a blocked state,
      the expansible part is provided at the inside of the front end part of the plunger, and
      the front end part of the plunger is inserted into the barrel while the plunger is inserted into the barrel.

2. The epidural space identification device according to claim 1, wherein
   the expansible member further comprises:
      an outer circumferential part that fits to an outer circumferential surface of the front end part of the plunger and slidably contacts an inner circumferential surface of the barrel,
      an engagement protrusion that engages with an engagement groove formed on the outer circumferential surface of the front end part of the plunger, and
      a proximal end part of the expansible member that contacts a front end of the plunger,
   and the expansible part that bulges inside of the plunger is continuous with the proximal end part of the expansible member.

3. The epidural space identification device according to claim 2, wherein:
   the expansible member further comprises a cylindrical inner part formed at an inner end of the proximal end part of the expansible member so that the cylindrical inner part fits to an inner circumferential surface of the plunger, and
   the expansible part is provided on a base end of the cylindrical inner part of the expansible member.

4. The epidural space identification device according to claim 3, wherein the air hole is formed at a base end surface of the plunger.

5. The epidural space identification device according to claim 2, wherein the air hole is formed at a base end surface of the plunger.

6. The epidural space identification device according to claim 1, wherein the air hole is formed at a base end surface of the plunger.

* * * * *